United States Patent

Wood et al.

[11] Patent Number: 5,933,245
[45] Date of Patent: Aug. 3, 1999

[54] PHOTOACOUSTIC DEVICE AND PROCESS FOR MULTI-GAS SENSING

[75] Inventors: R. Andrew Wood, Bloomington; Thomas M. Rezachek, Cottage Grove; Rudy R. Hegel, Richfield, all of Minn.

[73] Assignee: Honeywell Inc., Minneapolis, Minn.

[21] Appl. No.: 08/778,382

[22] Filed: Dec. 31, 1996

[51] Int. Cl.$^6$ .......................... G01N 21/61; G01N 21/03
[52] U.S. Cl. .................. 356/437; 356/246; 356/432; 356/440
[58] Field of Search .................... 356/432, 437, 356/438, 439, 440, 246

[56] References Cited

U.S. PATENT DOCUMENTS

| | | | |
|---|---|---|---|
| 3,938,365 | 2/1976 | Dewey, Jr. | 73/24 |
| 4,044,257 | 8/1977 | Kreuzer | 356/432 |
| 4,273,450 | 6/1981 | Watanabe et al. . | |
| 4,323,777 | 4/1982 | Baskins et al. . | |
| 4,419,211 | 12/1983 | Brauer . | |
| 4,437,005 | 3/1984 | Ophoff et al. . | |
| 4,457,162 | 7/1984 | Rush et al. | 73/24 |
| 4,557,137 | 12/1985 | Kitamori et al. . | |
| 4,557,603 | 12/1985 | Oehler et al. . | |
| 4,657,397 | 4/1987 | Oehler et al. . | |
| 4,709,150 | 11/1987 | Burough et al. . | |
| 4,740,086 | 4/1988 | Oehler et al. . | |
| 4,818,882 | 4/1989 | Nexo et al. . | |
| 4,866,681 | 9/1989 | Fertig . | |
| 5,163,332 | 11/1992 | Wong . | |
| 5,394,934 | 3/1995 | Rein et al. . | |

FOREIGN PATENT DOCUMENTS

| | | |
|---|---|---|
| 0590813 | 4/1994 | European Pat. Off. . |
| 3707622 | 9/1988 | Germany . |
| 44 32 819 | 4/1995 | Germany . |
| 4446390 | 7/1996 | Germany . |
| 3509532 | 9/1996 | Germany . |
| WO 96/02820 | 2/1996 | WIPO . |

OTHER PUBLICATIONS

"Opto–Acoustic Spectroscopy", Dewey, Jr., *Optical Engineering*, Nov./Dec. 1974, vol. 13, No. 6, pp. 483–488.
"A Simple Device For Trace Gas Analyses In The Atmosphere", *Journal De Physique*, Oct. 1983, pp. 587–591.
"A simple photoacoustic gas–detection system", *Rapport de la reunion d'autonne de la Societe Suisse de Physique*, vol. 54, 1981, pp. 631–635.

*Primary Examiner*—Richard A. Rosenberger
*Attorney, Agent, or Firm*—Ian D. MacKinnon

[57] ABSTRACT

A photoacoustic gas sensing system includes either separate lasers or an arrangement of emitters and filters, to provide infrared energy within at least two distinguishable frequency bandwidths, modulated at two or more associated and different modulating frequencies. The modulated energy signals illuminate a gas cell containing a mixture of gases that experience temperature and pressure fluctuations responsive to the radiant energy. An amplified microphone signal, produced responsive to the pressure fluctuations, is detected at the different modulation frequencies to provide two or more detector signals in digital form. These signals are processed in combination with predetermined constants derived by calibrating the system, to generate two or more concentration values corresponding to the individual gases involved. The system can utilize a photoacoustic cell with walls formed entirely of a polymer that is both gas-permeable and transparent to the infrared radiation. If desired, a temperature sensor and a pressure sensor near the cell provide respective signals based on ambient temperature and ambient pressure. These ambient condition signals are used to provide concentration measurements corrected for changes in ambient temperature and pressure, including pressure differences due to differences in elevation. Temperature and light sensors can be included to reduce temperature-dependent and time-dependent variations in sensor calibration.

2 Claims, 4 Drawing Sheets

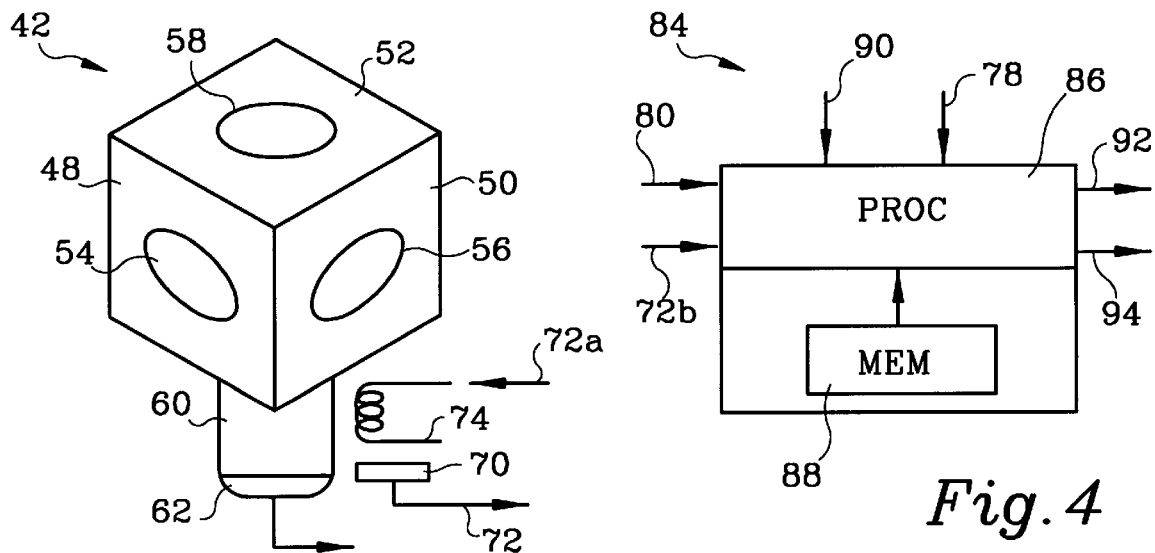
Fig.3
Fig.4
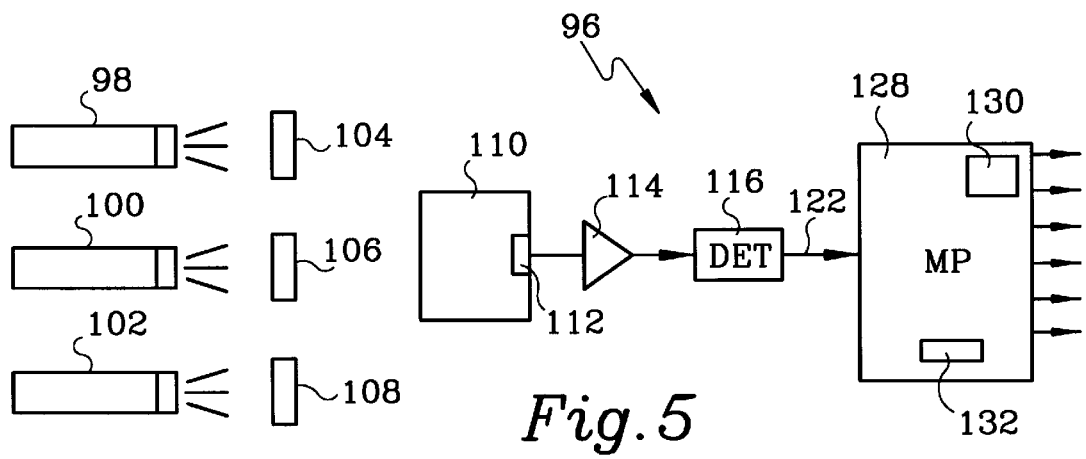
Fig.5
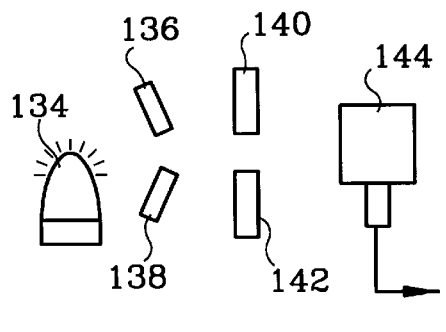
Fig.6

PHOTOACOUSTIC DEVICE AND PROCESS FOR MULTI-GAS SENSING

BACKGROUND OF THE INVENTION

The present invention relates to photoacoustic or optoacoustic spectroscopy, and more particularly to applications that involve measurement of two or more gases or vapors in a mixture.

Photoacoustic measurement is based on the tendency of molecules, when exposed to certain frequencies of radiant energy (e.g. infrared radiant energy), to absorb the energy and reach higher levels of molecular vibration and rotation, thereby to reach a higher temperature and pressure. When the radiant energy is amplitude modulated, the resulting fluctuations in energy available for absorption produce corresponding temperature and pressure fluctuations. A sensitive microphone can be used to generate an electrical output representing the pressure fluctuations. The amplitudes of the acoustic signal and resulting electrical output are proportional to the intensity of the radiation and the concentration value of the absorbing gas. Accordingly, given a constant amplitude of radiant energy illumination, the electrical output can be detected at the modulating frequency to provide a concentration value proportional to an absorbing amount of the gas. Further, the proportional relationship with light source intensity allows the user to increase sensitivity by increasing light source intensity. Thus the devices are well suited for measuring small concentration values of gases (ppm, i.e., parts-per-million range), especially as compared to sensors that rely on measurement of transmitted radiant energy.

A variety of these devices are known, e.g. see U.S. Pat. No. 4,557,603 (Oehler et al), U.S. Pat. No. 4,818,882 (Nexo et al), and U.S. Pat. No. 4,866,681 (Fertig). The devices have several components in common. In particular, a laser or other energy source produces radiant energy which is modulated either thermally (power on/off) or with a chopping device. The modulated energy is provided to a cell containing a gas or gas mixture that absorbs the radiant energy, leading to temperature fluctuations in the gas that track the modulation frequency. Temperature is not sensed directly. Rather, pressure fluctuations that accompany the temperature fluctuations are detected by a sensitive microphone in the cell. The microphone output is detected at the modulation frequency, to provide an electrical signal proportional to the gas concentration.

Frequently there is a need to determine the concentrations of two or more gases within a gas mixture. While this could be accomplished with two or more sensing systems, one devoted to each of the gases under study, a sharing of components among several systems would likely reduce costs. Accordingly there have been several proposals involving use of a single photoacoustic cell to detect two or more gases.

For example, the Nexo et al patent discloses a perforated disk with three sets of filter openings with different spacings between adjacent openings, for simultaneously: (1) filtering infrared light into different wavelengths "absorbed by $N_2O$, $CO_2$, and anesthetics, respectively"; and (2) modulating the wavelengths at three different frequencies. Signals corresponding to the various gases are said to be separated through an electric filtration of the microphone signal.

The Oehler et al patent discloses a mechanical light modulator and monochromator having different interference filters said to enable simultaneous separate detection of several components of a gas mixture. Oehler indicates that the interference with measurement by other gas components can be largely eliminated by using more than one narrow-band filter adapted to the maxima or flanks of the measuring gas or interfering components. Concentrations of different components are said to be determinable from the measurements performed with the different narrow band filters, with these filters being successively introduced into the path of the rays.

One disadvantage of these systems is the need to provide the radiant energy in extremely narrow bands. This requires either lasers for generating energy, or equipment designed to successively introduce different narrow-band filters into the light path between the source and photoacoustic cell. Either approach adds to the cost of the system. Further, it is difficult within the confines of these systems to distinguish between two gases with overlapping or coinciding absorption bands, or to determine the presence of an unknown absorbing gas.

Therefore, it is an object of the this invention to provide for the simultaneous sensing of two or more gases by: using shared components, e.g. a single photoacoustic cell, microphone and amplifier; avoiding the need to generate radiant energy solely as monochromatic beams; and using no moving parts.

Another object is to provide the capability of separately measuring the concentration values of several gases having absorption lines or bands which may overlap or coincide with one another, or detecting the presence of another gas whose absorption bands or lines may overlap or coincide with those of the several gases whose sensing is desired.

Another object is to render the sensor more reliable, by correcting concentration values for effects of varying temperature, atmospheric pressure, and elevations of installed sensors relative to sea level.

SUMMARY OF THE INVENTION

To achieve these and other objects, there is provided a photoacoustic gas sensing system. The system includes a radiant energy source for generating radiant energy in respective first and second frequency bandwidths. The source provides the radiant energy to a measuring region occupied by a gas mixture that includes first and second different gases. A modulating means modulates the radiant energy at first and second modulating frequencies associated with the first and second frequency bandwidths, respectively, to provide the radiant energy in the form of first and second modulated energy signals. A transducing means at the measuring region simultaneously receives the first and second modulated energy signals; and in response, generates a transducer signal. A detecting means is coupled to the transducing means, for detecting the transducer signal to produce a detector output comprised of a first signal component at the first modulating frequency, and a second signal component at the second modulating frequency. A signal processing means is coupled to receive the detector output, and combines the first and second signal components individually with predetermined constants based on radiant energy absorbing characteristics of the first and second gases, to generate first and second concentration value indicating, respectively, a concentration of the first gas and a concentration of the second gas within the measuring region.

Preferably the processing means includes a digital memory for storing the predetermined constants. For determining the concentrations of two gases, up to six constants are stored. Constants a, b, c and d relate to the tendency of each of the first and second gases individually to absorb energy in each of the first and second frequency bandwidths. Two further constants e and f relate to the tendency of the of the cell walls and windows to absorb energy in the first and second frequency bandwidths. Then, the detector signals are provided to the processing means as binary signals. A processing circuit in the processing means combines the constants a–d and the detector signals to compute the first and second concentration values according to the following equations:

$$X = \frac{dS_1 - bS_2 - de + bf}{da - bc}; \text{ and } Y = \frac{aS_2 - cS_1 - af + ec}{da - bc};$$

where $S_1$ is the first detector signal, $S_2$ is the second detector signal, X is the concentration value associated with the first gas and Y is the concentration value associated with the second gas.

The constants are obtained in a calibration procedure that uses known concentrations of the first and second gases.

The constants differ from one another in a manner that reflects the unique absorptivity characteristics of each gas. More particularly, radiant energy absorption spectra of gases typically feature narrow bands of high absorptivity, spaced apart from one another by regions of substantially lower absorptivity. Each gas has its own unique spectrum, i.e. pattern of high absorptivity and low absorptivity regions within a given range of radiant energy wavelengths.

This approach does not require that all of constants a–f have the same or even a substantial impact on the determinations of X and Y. For example, one of constants a–d may be negligible and treated as zero in the above equations, in cases where one of the first and second frequency bandwidths is narrow, or in cases where one of the first and second gases absorbs negligible energy in one of the first and second frequency bandwidths despite its breadth. One or both of constants e and f may be negligible and treated as zero, in cases where the cell structure absorbs little or no energy in the first and/or second frequency bandwidths. Such cases notwithstanding, frequently all of constants a–f play a substantial role in determining concentration values X and Y.

The above two equations are employed to solve for two unknowns, and thus allow simultaneous determination of two gas concentration values. The approach requires only one cell, one microphone, one amplifier, one digital processor, and requires no moving parts. The same signal processing circuitry accommodates all incoming signals. The composite contribution of separate gases is taken into account. Therefore, there is no need to generate precise and narrow separate bandwidths for the separate gases, in an attempt to provide that each of the gases absorbs only one of the frequency bandwidths used to determine concentrations. One or both of these bandwidths can be made much broader and the bandwidths even can overlap one another (although they cannot be identical), since there is no need to isolate a given bandwidth for absorption by only one of the gases. Each bandwidth should be chosen to broadly coincide with the absorption bands of each gas desired to be sensed. The use of broader wavebands increases sensitivity while at the same time reducing cost. The bandwidths need not coincide with particular high absorptivity bands of the gases involved. However, they may coincide without causing error.

A further advantage arising from the calibration and processing involved, is that radiant energy can be provided at a third frequency bandwidth modulated at a third modulating frequency, with up to three further constants determined by calibration, and stored. Then, the transducer signal can be detected at the third modulating frequency to produce a third detector output. The resulting nine constants can be used to redundantly calculate the concentration values of the first and second gases, for enhanced reliability. Alternatively, differences between redundant determinations of the concentration values can be used to determine the presence of an unknown gas. According to a further alternative, three further constants are determined by calibration and stored, and the resulting twelve constants used to find concentration values of three different gases.

Consistent with the preference for processing digital data to determine concentration values, the detecting means can include analog-to-digital converters, so that the detector outputs are digital values. The detector also includes a clocking means to ensure that the detector outputs are in phase with one another.

Structural components of the photoacoustic sensing system can be varied within the scope of the invention. For example, the radiant energy source can comprise two or more emitters of coherent infrared energy at the different frequency bandwidths. Alternatively, one or more broadband sources are employed in combination with two or more filters. The modulating means can include one or more disks between the source and measuring region, each disk having openings and rotatable to alternatively pass and block the radiant energy at a chosen modulating frequency. When the source includes two or more emitters, the emitters can be thermally modulated.

The preferred transducing means comprises a cell containing the gas mixture. At least part of the cell wall is transparent to radiant energy in the first and second energy bandwidths, to ensure that absorption occurs whenever the cell is exposed to energy in either bandwidth. One part of the cell wall can be gas permeable as well.

Certain options are preferred to ensure reliable operation over extended time periods, and over a range of operating temperatures, and ambient pressures. Long term operation is enhanced by providing a light sensor near the radiant energy source. The sensor can be employed either to trigger an adjustment to the IR source to maintain uniform intensity, or to govern an input to the digital processor to compensate for a change (typically a decrease) in source intensity.

For improved performance over a wide temperature range, a temperature sensor can be positioned near the microphone, to counteract the effects of microphone temperature sensitivity. The sensor output can be used to control a heating element near the microphone, thus to maintain the microphone at a uniform temperature. Alternatively the sensor output can be provided to the digital processor to correct for the effects of changes in the microphone temperature.

For improved performance over a range of sensor locations (specifically elevations relative to sea level), ambient air temperatures and ambient pressures, a pressure sensor and a temperature sensor can be used to provide signals to the digital processor, proportional respectively to ambient pressure and ambient temperature, thus to provide concentration measures corrected for the effects of sensor elevation, changes in atmospheric pressure and changes in ambient temperature.

Accordingly, further in accordance with the present invention there is provided a photoacoustic gas sensing system including a radiant energy source for generating radiant energy and providing the radiant energy to a measuring region occupied by a gas mixture. The system further includes a modulating means for modulating the radiant energy to provide radiant energy to the measuring region as a modulated energy signal. A transducing means at the measuring region receives the modulated energy signal and in response generates a transducer signal. A detecting means is coupled to the transducing means and detects the transducer signal to produce a detector output at the modulating frequency. A sensor, located near the measuring region, detects an ambient condition and generates a sensor output that depends on the ambient condition. A signal processing means, coupled to receive the detector output and the sensor output, generates a concentration value indicating a concentration of a gas within the measuring region, corrected for variations in the ambient condition.

The ambient condition can be atmospheric pressure, ambient temperature, or both. In this latter, preferred case, a temperature sensor and a pressure sensor are located at the measuring region, and provide respective temperature sensitive and pressure sensitive signals to the signal processing means.

As a further option, the cell can be composed of a wall formed entirely of a gas permeable material that also is transparent to radiant energy in the first and second frequency bands. In this structure, a gas permeable and radiant energy permeable polymer forms the entire cell wall structure, rather than merely providing gas and energy permeable windows through windows formed in a structural material such as aluminum. The result is an increase in efficiency due to the greater surface area of permeable material for a cell of a given volume, whereby gases more readily permeate through the cell wall and a higher proportion of the radiant energy is transmitted into the cell. Moreover, the cell is less expensive, due to reductions in material and manufacturing costs.

Thus in accordance with the present invention, a single photoacoustic cell can be used to determine simultaneously the concentrations of two or more gases by processing the transducer signal in a manner that takes into account the contribution of each gas to the pressure fluctuations. A single transducer signal, produced as a function of the cumulative pressure fluctuations, is detected at the same modulating frequencies used in illuminating the cell with the different radiant energy bandwidths. Typically, each of the resulting detector signals is influenced by all of the gases under study. When the detector signals are processed in conjunction with predetermined constants and as discussed above, the result is a set of values individually associated with the individual gases in the mixture.

IN THE DRAWINGS

For a further understanding of these and other features and advantages, reference is made to the following detailed description and to the drawings, in which:

FIG. 3 is a perspective view of a photoacoustic transducing cell of the system;

FIG. 4 is a schematic view of a digital processing device of the system;

FIG. 5 is a diagrammatic view of an alternative embodiment photoacoustic gas sensing system constructed according to the present invention;

FIG. 6 is a schematic view of an alternative embodiment source of modulated radiant energy for use in either photoacoustic system.

DETAILED DESCRIPTION OF THE PREFERRED EMBODIMENTS

Figure 1:
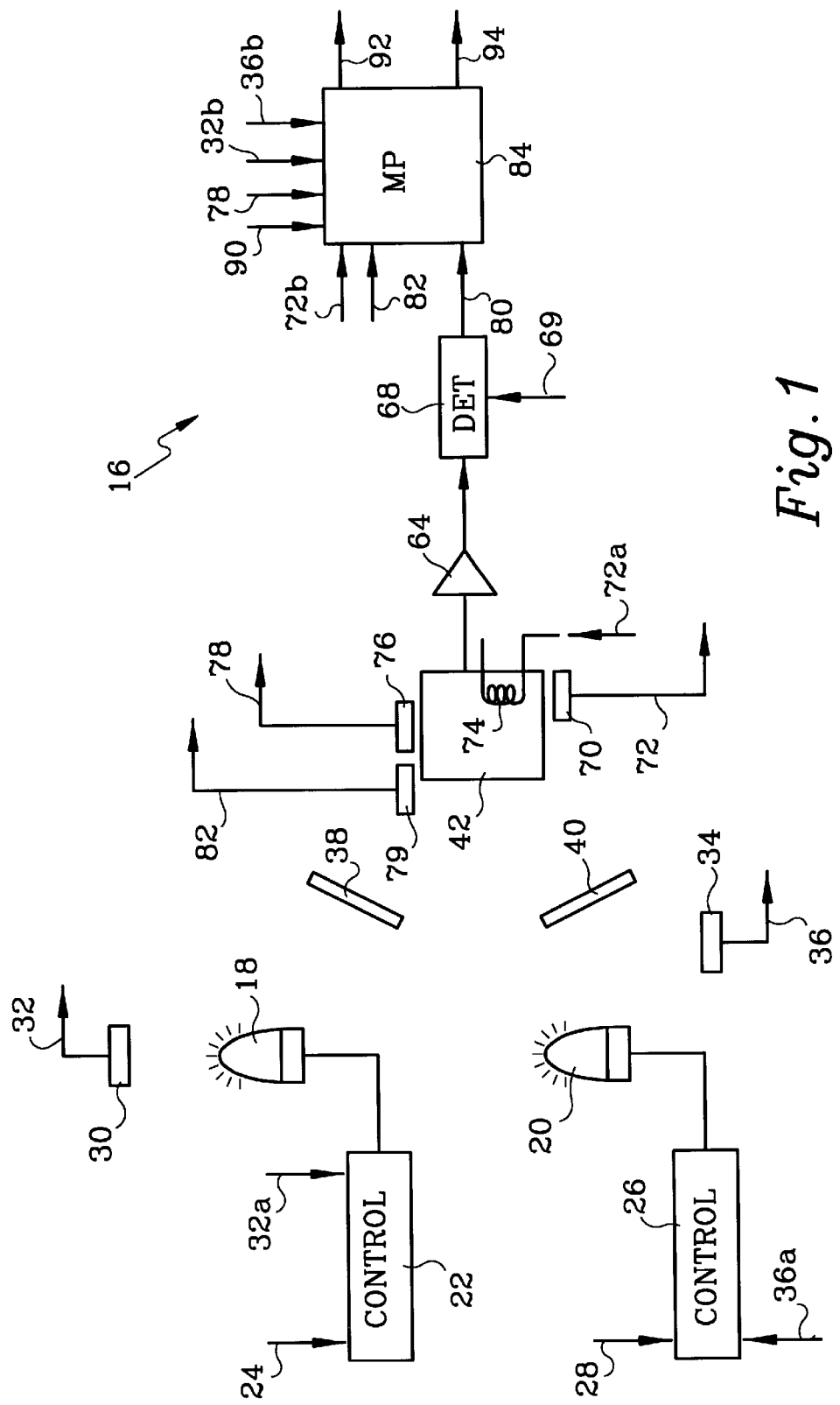
FIG. 1 is a diagrammatic view of a photoacoustic gas sensing system constructed according to the present invention.

Turning now to the drawings, there is shown in FIG. 1 a photoacoustic gas sensing system 16 for sensing gases at a selected measuring region. The system is adapted to simultaneously determine the concentration values of two different gases, and to this end employs: (a) a radiant energy source that provides radiant energy in two distinct frequency bandwidths, modulated at two different frequencies; (b) a single transducing arrangement that generates an analog electrical output responsive to receiving the radiant energy; and (c) signal processing circuitry that detects and analyzes the analog electrical signal to produce two outputs, one corresponding to the concentration value of each gas.

Figure 2:
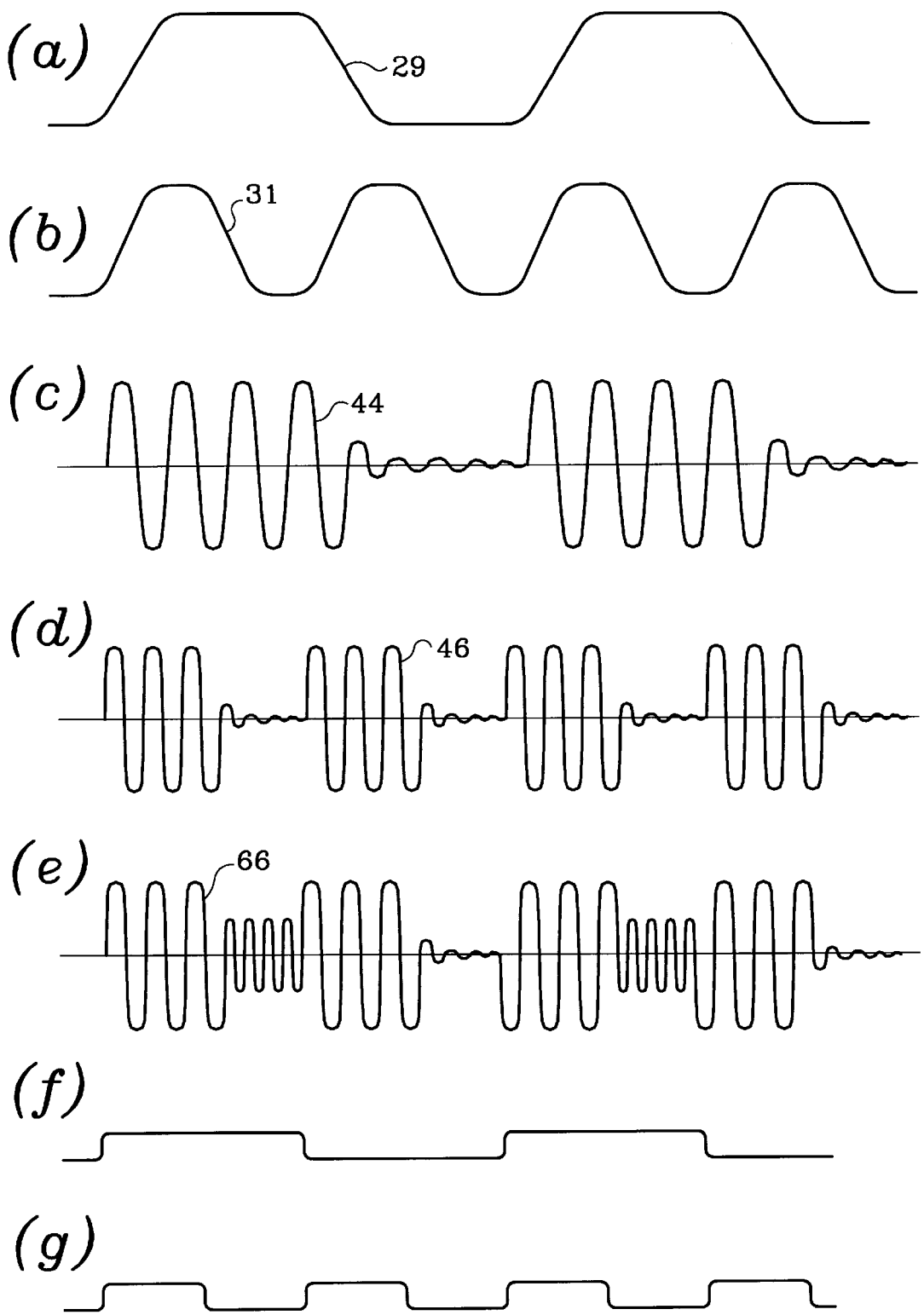
FIG. 2 is a timing diagram illustrating signals at different ages throughout the system.

More particularly, the radiant energy source includes two spaced apart low power (e.g. 0.5 w) lamps or emitters 18 and 20 that produce broadband radiant energy, preferably in the infrared range. A controller 22 is coupled to emitter 18. Governed by a digital timing input 24, controller 22 thermally modulates emitter 18, i.e. cyclically activates and deactivates emitter 18 at a first modulating frequency, e.g. about ten Hz. Emitter 20 likewise is coupled to a controller 26 which is governed by a timing input 28. Controller 26 thermally modulates emitter 20 according to a second modulating frequency that is distinct from the first modulating frequency; e.g. about eight Hz. The first and second modulating frequencies are shown at 29 and 31 in FIG. 2. The two modulation frequencies should not be harmonics of each other, and should not be extremely close to each other. FIG. 2 illustrates the fact that the modulation frequencies are different, and is not intended to show precisely a ratio or other relationship between these frequencies.

A sensor 30 generates an output 32 as a function of the amplitude of the infrared energy from emitter 18. Similarly, a sensor 34 generates an output 36 responsive to emitter 20. The sensor outputs can be used to counteract or compensate for the tendency of emitters 18 and 20 to generate infrared energy at an intensity that diminishes gradually over time. More broadly, outputs 32 and 36 can be used to compensate for or counteract any change in radiant energy intensity.

Inputs 32a and 36a to controllers 22 and 26, respectively, illustrate the use of outputs 32 and 36 to adjust the power to emitters 18 and 20, e.g. by increasing power to an emitter responsive to sensing a decrease in the intensity or amplitude of the emitted energy. This better ensures that emitters 18 and 20, over an extended time period, emit energy at uniform intensities. Alternatively, the sensor outputs can be provided to a microprocessor, as indicated at 32b and 36b in FIG. 1. Inputs 32b and 36b to the microprocessor ensure that calculated gas concentration values reflect compensation for changes in emitter intensity.

The efficiency at which a gas absorbs radiant energy fluctuates considerably with the radiation frequency of the energy. Energy absorption by a particular gas over a frequency spectrum typically includes narrow bands or lines of high absorptivity, spaced apart from one another by frequency bands of much lower absorptivity. Each gas has a unique absorptivity spectrum. Accordingly, photoacoustic systems can be enhanced by tailoring the radiant energy frequencies to the gases under study. To this end, a filter 38 disposed near emitter 18 transmits the radiant energy only within a somewhat narrowed waveband or first frequency bandwidth. Likewise, a filter 40 near emitter 20 transmits energy only within a second frequency bandwidth different from the first frequency bandwidth. The first and second frequency bandwidths, both within the infrared range, can overlap one another but cannot be identical. Each frequency bandwidth should be chosen to broadly coincide with the strongest absorption bands of each gas to be sensed. In the case of water vapor (humidity) and carbon dioxide ($CO_2$), the first frequency bandwidth can include a range from about 1 to about 5 micrometers, corresponding well to water vapor absorption, and the second frequency bandwidth may include a range from about 4 to about 5 micrometers, which corresponds well to carbon dioxide absorption.

In one particular example, a sensor for measuring the concentration of carbon dioxide and humidity in air included the following energy sources and filters for providing the different wavebands at low cost: a flashlight bulb with a glass IR filter to provide a first frequency bandwidth of high intensity from about 0.5 micrometers to about 5.0 micrometers; and a flashlight bulb and glass filter, in combination with a further IR filter consisting of several alternating layers of germanium and silicon dioxide deposited on silicon. This combination provides a second frequency bandwidth of lower intensity from about 1.2 micrometers to about 4.0 micrometers, and relatively high intensity from about 4.0 micrometers to about 5.0 micrometers.

A transducer responsive to the infrared energy, typically a photoacoustic cell 42, is positioned to receive filtered energy from both emitters 18 and 20. In each case, the energy received at cell 42 represents the output of the emitter, modulated by the associated controller and narrowed as to frequency (or wavelength) range by the associated filter. Thus, cell 42 receives energy in the form of respective amplitude modulated energy signals 44 and 46, shown in FIG. 2. In each of signals 44 and 46, the frequency of the carrier is much higher than the modulating frequency, in particular by about twelve orders of magnitude or more. Accordingly, the composite or modulated signals precisely replicate their associated modulating signals.

Photoacoustic cell 42 is shown in more detail in FIG. 3. Cell 42 has a wall structure, preferably aluminum or another metal, that encloses a generally cube-shaped measuring region or volume of about one cc. The wall structure includes separate generally planar sections, with side wall sections 48 and 50 and a top wall section 52 visible in the figure. Openings 54 and 56 through wall sections 48 and 50 are covered with a material transparent to infrared radiation, e.g. glass. Other choices include germanium and sapphire. An opening 58 through top wall section 52 is covered by a porous membrane formed of paper, a porous metal or a polymer, which is gas permeable. Thus, after a brief time (e.g. about 5 minutes) within a given environment, the measuring volume within the cell, typically about one cubic centimeter, substantially matches the characteristics of the gas mixture in the surrounding environment.

A detector sensitive to acoustic signals, i.e. an electret microphone 60, is mounted within a bottom wall section and is exposed to the cell interior, and also has a terminal end 62 that extends outwardly beneath the cell. In combination, cell 42 and microphone 60 function as a transducing means for generating an analog electrical output responsive to simultaneous reception of modulated energy signals 44 and 46.

Briefly, as gases inside the cell absorb the incoming radiant energy, individual molecules experience increased rotation and vibration, and the collisions among molecules increase. This activity is manifested as a temperature increase and, with the gas being essentially contained within the measuring volume, a pressure increase as well. Because the infrared energy is received as two amplitude modulated signals, the temperature and pressure within the cell fluctuate. The pressure fluctuations produce an acoustic signal, which is received by microphone 60 for generating the analog electrical output. An amplifier 64 (FIG. 1) amplifies the microphone output to produce a transducer signal 66 shown schematically in FIG. 2. Because of the different modulating frequencies involved, the transducer signal is a combination of signals at both modulating frequencies.

The amplified transducer signal is provided to a detector 68. A timing input 69 governs detection according to the modulating frequencies, represented digitally at (f) and (g) in FIG. 2. The detector produces a digital representation of the transducer signal. The digital representation includes respective signal components at the first and second modulating frequencies. This digital representation is provided to a digital processor, i.e. a microprocessor 84. The microprocessor digitally computes the modulus of the amplitude of each modulating frequency component, by a lock-in algorithm, and averages the resulting amplitudes for a selected period (about one minute) to smooth noise.

As seen in FIG. 4, the microprocessor includes processing circuitry 86 and a memory 88. The memory stores six constants a–f. The constants are obtained by calibrating photoacoustic cell 42 with reference to the pair of gases to be measured, and with reference to the first and second frequency bandwidths illuminating the cell. Calibration involves illuminating the cell, at each of the first and second frequency bandwidths, when the cell contains known concentrations of the gases under study and an inactive gas chosen for non-absorptivity of the particular frequency bandwidth, e.g. nitrogen. The resulting constant "a" reflects the tendency of the first gas to absorb infrared energy at the first frequency bandwidth. Constant "b" reflects the tendency of the second gas to absorb energy in the first frequency bandwidth; and constants "c" and "d" respectively reflect the tendencies of the first and second gases to absorb energy in the second frequency bandwidth. If one frequency bandwidth is a narrow bandwidth, or if one gas has negligible absorption in one radiation bandwidth, one or more of the above constants may have a negligible value or be zero. The constant "e" is a fixed offset value accounting for the fact that the walls and windows of photoacoustic cell 42 absorb energy within the first frequency bandwidth. Similarly, the constant "f" accounts for such absorption of energy in the second frequency bandwidth.

Detector 68 provides an output or composite signal 80 containing components at both of the modulating frequencies, due to the absorption of energy in both infrared wavebands, by both gases. This phenomenon is represented by the following equations:

$$S_1 = aX + bY + e; \text{ and}$$

$$S_2 = cX + dY + f;$$

where $S_1$ is the signal component at the first modulating frequency, $S_2$ is the signal component at the second modulating frequency, "X" is the concentration value of the first gas, and "Y" is the concentration value of the second gas. These equations, when solved for the respective concentration values, become:

$$X = \frac{dS_1 - bS_2 - de + bf}{da - bc}; \text{ and } Y = \frac{aS_2 - cS_1 - af + ec}{da - bc}.$$

Thus, "X" and "Y" are values indicating, respectively, the concentration values of the first and second gases within cell 42. Values "X" and "Y" can be provided simply as numbers proportional to their respective absorbing amounts, or can be converted to other measures of concentration.

A manipulation of detector signal 80 equivalent to solving the above equations, is accomplished by processing circuit 86. Along with receiving the detector signals as inputs, the processing circuit fetches constants a–f. The processing circuit is governed by a timing input 90, derived from the same clocking source governing the other timing inputs to ensure phase coherence. The processing circuit further receives sensor outputs 32 and 36 (as indicated at 32b and 36b), to accommodate differences in amplitude between emitters 18 and 20 and adjust for any diminishing in the amplitude of either emitter. Alternatively, the outputs are provided as control signals (32a and 36a) to maintain the amplitudes of the emitters at constant levels.

The phrase "concentration value" is used herein to denote a measured signal corresponding to the number of gas molecules in the gas cell. The concentration value does not depend on gas concentration alone, but can vary with changes in ambient temperature and ambient pressure. The location of photoacoustic cell 42 (in particular its elevation relative to sea level) influences pressure due to the tendency of atmospheric pressure to diminish with increasing elevation. Accordingly, the need arises to correct concentration values for temperature and pressure differences. To allow conversion of concentration values X and Y to concentration measures dependent upon air temperature and pressure, an air temperature sensor 76 generates a signal 78 (FIG. 1), and air pressure sensor 79 generates a signal 82. Signals 78 and 82 are provided as inputs to microprocessor 84. Thus, processor outputs 92 and 94 represent the respective concentration measures, i.e. the concentration values corrected for ambient temperature and pressure (including elevation). The concentration measures can be provided to a video terminal, printer or other peripheral device (not shown), to provide readable practical measures in terms of ppm or relative humidity. Or, the concentration measures can be provided to a device for triggering an alarm responsive to an undesirably high concentration of either gas.

Microphone 60 is sensitive to changes in temperature. Accordingly, where system 16 is expected to operate over a wide temperature range, such sensitivity is either nullified by maintaining a substantially constant microphone temperature, or compensated in microprocessor 84.

Presently the preferred approach is to maintain a constant microphone temperature. To this end, a temperature sensor 70 is fixed near the microphone and preferably inside of the photoacoustic cell, although sensor 70 can be outside of the cell as shown in FIGS. 1 and 3. A temperature sensor output 72 is provided as an input to a heating element 74 near the microphone as indicated at 72a, thus providing a control to maintain microphone 60 at a selected temperature. The response of gases in cell 42 to the heating element is negligible; i.e. microphone 60 is heated without introducing an error into the concentration values.

As a suitable alternative, sensor output 72 is provided to microprocessor 84 as an input 72b to processing circuit 86. Consequently, processor outputs 92 and 94 are generated in a manner that compensates for temperature induced changes in microphone sensitivity. Given the further inputs from temperature sensor 76 and pressure sensor 79 to the microprocessor, outputs 92 and 94 are generated to correct for fluctuations in ambient conditions, as well.

A salient feature of detecting system 16 is that a single transducer output, based on a composite of two different gases responding to two different radiant energy inputs, is processed to yield two separate concentration values, each individually related to one of the gases under study. There is no need to confine the first and second frequency bandwidths to extremely narrow, mutually exclusive frequency ranges, each range specially tuned toward absorption exclusively by one of the gases involved. Such an ideal is difficult to achieve or approach, due to the tendency of each gas to absorb radiation at the bandwidth chosen "exclusively" for the other gas.

The present invention involves taking this tendency into account, rather than straining to avoid it. First, because the radiant energy bandwidths need not be so strictly confined and narrow, much less costly radiant energy emitters can be used. While two different concentration values are obtained, they are obtained from the same microphone output using the same processing circuitry. A further advantage is the increased sensitivity which results from providing the radiant energy at broader frequency bandwidths. Finally, more flexibility results because the different infrared frequency bandwidths can overlap one another, to the point of sharing one or more of the high absorptivity bands of the involved gases. Coincident absorption lines do not cause error.

Taking into account the tendency of each gas to affect responses of the other gases to incoming radiant energy, affords further advantages when a photoacoustic cell is illuminated with three or more different frequency bandwidths of the radiant energy. FIG. 5 illustrates a photoacoustic detecting system 96 in which three lasers 98, 100 and 102 generate infrared energy at three coherent frequency bandwidths (or wavelengths). Accordingly, there is no need for individual filters such as 38 and 40 of system 16. In system 96, the radiant energy is modulated mechanically rather than thermally. In particular, disks 104, 106 and 108 are interposed between a photoacoustic cell 110 and lasers 98, 100 and 102, respectively. The disks have regularly spaced apart openings, e.g. as disclosed in the aforementioned U.S. Pat. No. 4,818,882. Consequently when each of the disks is rotated, energy from its associated laser is "chopped" or modulated at a modulation frequency that depends on the disk rotational speed.

Cell 110 includes a microphone 112 for generating an analog electrical output that is amplified by an amplifier 114. The amplifier output is provided to a detector 116 for detection of the analog signal at the three different modulating frequencies, thus to provide a detector output 122 to a microprocessor 128. Microprocessor 128 includes circuitry for computing the modulus of the amplitude of each modulating frequency component of signal 122.

The microprocessor includes a processor circuit 130 and a memory 132, substantially similar to their counterparts in microprocessor 84. Memory 132, however, stores nine constants a-i, with additional constants g, h and i based on the respective tendencies of the first gas, the second gas and the cell structure to absorb energy in the third frequency bandwidth.

The additional radiant energy bandwidth and modulating frequency enable redundant sensing and processing, to yield three equations for concentration value "X" and three equations for concentration value "Y". The redundant calculations provide a check on the initial calculations for enhanced reliability.

Alternatively, differences among the concentration values can be used to determine the presence of an unknown gas that is causing unequal contributions to the separate detector signals. Calibration occurs as explained above, the only difference being the additional calibrations associated with the third frequency bandwidth.

As a further option, system 96 can be calibrated in view of three different test gases, to provide twelve constants a–l that collectively reflect the tendency of each of the three gases and the cell structure to absorb energy in each of the three frequency bandwidths. While the governing equations and resulting processor circuitry (or programming) are somewhat more complex, the above-discussed advantages are more pronounced as compared to the two-gas system.

FIG. 6 illustrates and alternative radiant energy source that uses a single lamp or broadband emitter 134, in combination with two filters 136 and 138 and two disks or choppers 140 and 142. Filters 136 and 138, like their counterparts 38 and 40 in system 16, transmit light from emitter 134 respectively as first and second different frequency bandwidths. Disk 140 modulates energy in the first frequency bandwidth at a first modulating frequency, and disk 142 modulates energy at the second frequency bandwidth at a second modulating frequency different than the first. Mirrors or other components are suitably arranged to ensure that a photoacoustic cell 144 receives only the composite of energy in the first frequency bandwidth modulated at the first modulating frequency and energy in the second frequency bandwidth modulated at the second modulating frequency. Downstream amplification and processing of the transducer signal is substantially the same as described in connection with system 16.

Figure 7:
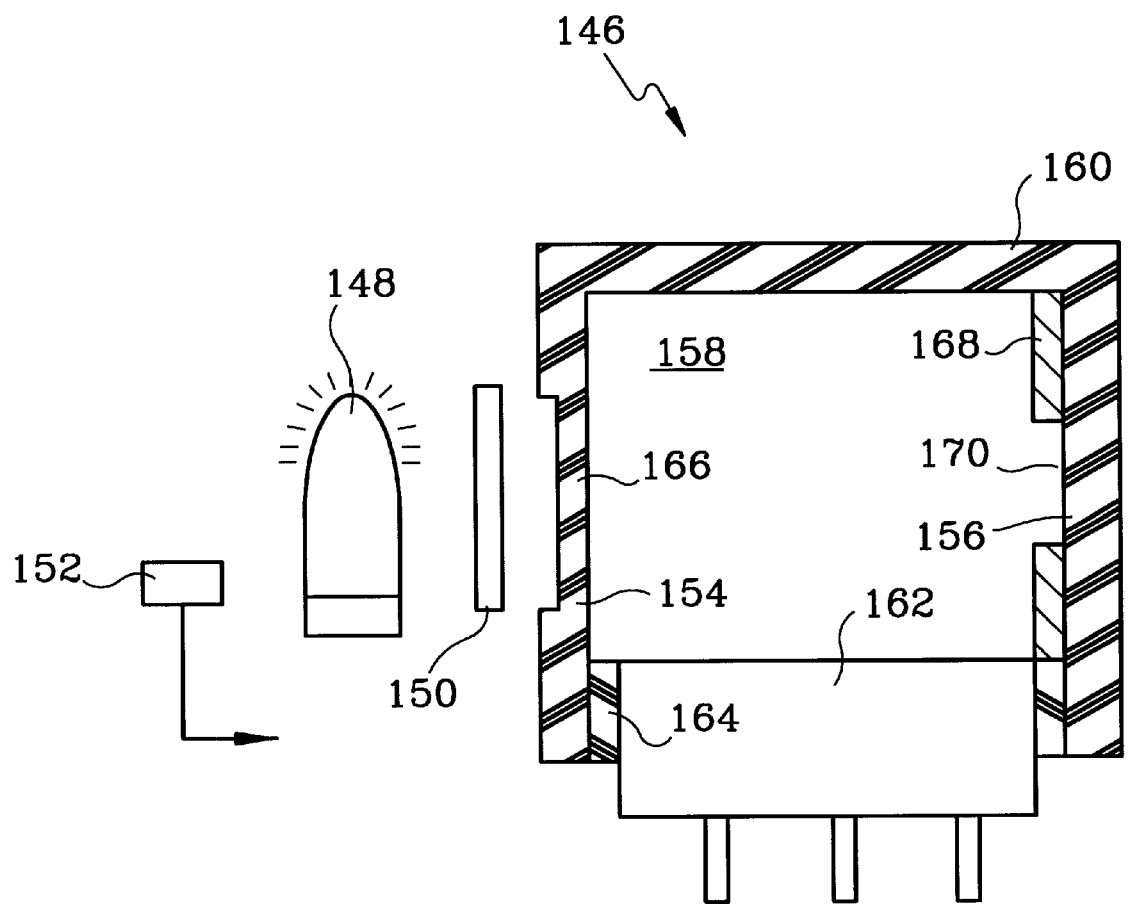
FIG. 7 is an elevational view in section of an alternative embodiment photoacoustic transducing cell usable in either of the systems.

FIG. 7 illustrates an alternative optoacoustic or photoacoustic gas cell 146 for use in either system 16 or 96, and a radiant energy source near the cell. The radiant energy source includes a broadband lamp or emitter 148 and an infrared filter 150 between emitter 148 and cell 146. The emitter preferably transmits infrared energy at a wavelength of about 4.2 microns. A silicon sensor 152 generates an output responsive to the amplitude of radiant energy from emitter 148 over its complete wavelength band.

Photoacoustic cell 146 is composed of generally flat wall sections that together enclose a cubic measuring volume of about one cubic cm. The cell is illustrated in section to show four of the wall sections; three side wall sections 154, 156 and 158 and a top wall section 160. Forming the bottom of cell 146 is an electret microphone 162, secured to the side walls by an adhesive 164.

The top wall and side walls are formed entirely of a polymer (e.g. methacrylate) that is permeable to infrared radiation, and further is gas permeable. In particular the wall sections are permeable to carbon dioxide and water vapor. Wall sections 154, 156, 158 and 160 are given a thickness (preferably less than 0.5 mm) consistent with adequate structural support. Further, individual wall sections can be provided with narrowed portions, as indicated at 166 in connection with wall section 154, to improve transmission of the infrared energy into the cell. While only one such narrowing is shown in connection with a single infrared emitter, it can be appreciated that two or more such portions and emitters can be provided for sensing two or more gases.

Because it is constructed entirely of methacrylate or another polymeric material, photoacoustic cell 146 can be fabricated by a molding process, thus reducing fabrication costs as compared to an aluminum cell. The polymeric wall sections lack the reflectivity of aluminum wall sections. For a more preferred construction employing the polymer yet exhibiting enhanced reflectivity, the polymeric wall sections can be metallized as shown at 168, e.g. by evaporation deposition, surface spraying or applying a metal foil. The wall sections are not completely covered. Rather, masking or foil cutting is employed to leave defined gas permeable and radiation permeable windows 170, consisting of the polymer.

Thus in accordance with the present invention, two or more gases can be measured simultaneously using a single photoacoustic cell, without the need to confine the radiant energy to unduly narrow bandwidths, and indeed provide enhanced sensitivity because the respective bandwidths can be broader and can overlap. A single output of the photoacoustic transducer is detected at the different modulating frequencies at which the different radiant energy frequency bandwidths are modulated, in phase coherency to generate two or more detector signals. Although each of the detector signals may be influenced by more than one of the radiant energy frequency bandwidths, the detector signals are processed in combination with predetermined constants to yield separate concentration values, each individually associated with a gas under study. Signals representing ambient temperature and ambient pressure can be processed as well, to yield concentration measures corrected for variations in ambient temperature and pressure. The photoacoustic cell can be illuminated by radiant energy in a further frequency bandwidth modulated at a further modulating frequency, either to provide redundant concentration values, enable measurement of an additional known gas, or to determine the presence of an unknown gas within the photoacoustic cell.

What is claimed is:

1. A photoacoustic cell for use in determining gas concentrations, including:

a substantially continuous wall means for defining and substantially enclosing a measurement chamber, said wall means being substantially entirely formed of a gas permeable material transparent to radiant energy;

an acoustic transducer for generating electrical signals in response to acoustic signals, said acoustic transducer including a pressure sensitive portion for receiving acoustic signals and providing the corresponding electrical signals at an output terminal thereof;

a means for mounting the acoustic transducer with respect to the wall means, to position the transducer with said pressure sensitive portion within the chamber while positioning the output terminal outside of the chamber; and wherein at least one of the wall sections includes a peripheral region having a first thickness and an interior region having a second thickness less than the first thickness to enhance the transmittance of radiation into the chamber.

2. A photoacoustic cell for use in determining gas concentrations, including:

a substantially continuous wall means for defining and substantially enclosing a measurement chamber, said wall means being substantially entirely formed of a gas permeable material transparent to radiant energy;

an acoustic transducer for generating electrical signals in response to acoustic signals, said acoustic transducer including a pressure sensitive portion for receiving acoustic signals and providing the corresponding electrical signals at an output terminal thereof;

a means for mounting the acoustic transducer with respect to the wall means, to position the transducer with said pressure sensitive portion within the chamber while positioning the output terminal outside of the chamber; and a reflective metallic layer applied to an interior surface of said wall means, said reflective metallic layer covering a first portion of said interior surface while leaving a second portion of said interior surface exposed, whereby the wall means adjacent said first portion of the interior surface exhibits enhanced reflectivity, reduced gas permeability and reduced transparency to radiant energy.

* * * * *